(12) United States Patent
Dueva-Koganov et al.

(10) Patent No.: US 7,033,577 B2
(45) Date of Patent: Apr. 25, 2006

(54) IN VITRO PREDICTION OF SUNSCREEN PFA VALUES

(75) Inventors: Olga V Dueva-Koganov, White Plains, NY (US); James P. Sanogueira, Suffern, NY (US); Ovidiu Romanoschi, Edison, NJ (US); Barbara Donovan, Wayne, NJ (US)

(73) Assignee: Playtex Products, Inc., Westport, CT (US)

( * ) Notice: Subject to any disclaimer, the term of this patent is extended or adjusted under 35 U.S.C. 154(b) by 35 days.

(21) Appl. No.: 10/779,314

(22) Filed: Feb. 13, 2004

(65) Prior Publication Data

US 2004/0219684 A1    Nov. 4, 2004

Related U.S. Application Data

(60) Provisional application No. 60/506,833, filed on Sep. 29, 2003, provisional application No. 60/447,092, filed on Feb. 13, 2003.

(51) Int. Cl.
  *A61K 7/42* (2006.01)
  *A61K 7/44* (2006.01)
  *A61K 7/00* (2006.01)
  *A61B 5/05* (2006.01)

(52) U.S. Cl. .......................... 424/59; 424/60; 424/400; 424/401; 600/407

(58) Field of Classification Search ................ 250/372, 250/373, 474.1; 424/59, 60, 400, 401; 600/407; 702/28
See application file for complete search history.

(56) References Cited

U.S. PATENT DOCUMENTS 6,820,014 B1 *  11/2004  Ferrero et al. ................. 702/28

OTHER PUBLICATIONS

Kligman LH and Kligman AM. In: Lowe NJ, Shaath NA, Pathak MA eds. Sunscreens: Development, Evaluation and Regulatory Aspects. New York; Marcel Dekker, 1997: 117-137.
http://www.bccancer.bc.ca/HPI/Education/CMESkinCancer/PreExaminationReading/_Carcinogenesis.htm.
JCIA Technical Bulletin, JCIA Measurement Standard for UVA Protection Efficacy. Issued Nov. 21, 1995.
Chardon A, Moyal D, and Hourseau C. In: Lowe NJ, Shaath NA, Pathak MA eds. Sunscreens: Development, Evaluation and Regulatory Aspects, New York: Marcel Dekker, 1997: 559-582.
Moyal D, Chardon A and Kollias N. Photodermatol Photoimmunol Photomed 2000; 16: 250-255.
Wendel V, Klette E, and Gers-Barlag H. SOWF 2001, 127 (10): 12-30.
DGK (German Society for Scientific and Applied Cosmetics)—Task Force "Sun Protection". IFSCC Magazine 2002; vol. 5, No. 3: 161-166.
http://www.labsphere.com/tech_info/docs/SPF_of_Sunscreens.pdf.
IMS Seminar Series. 2001 SCC Florida Chapter Sunscreen Symposium. Apr. 25, 2002.

* cited by examiner

*Primary Examiner*—Shelley A. Dodson
(74) *Attorney, Agent, or Firm*—Ohlandt, Greeley, Ruggiero & Perle, L.L.P.

(57) ABSTRACT

An in vitro method for the prediction of in vivo UVA protection by a composition with sunscreen properties. The method includes the steps of: determining in vivo SPF; determining in vitro SPF based on the sunscreen's absorbance spectrum in the UV region; normalizing the absorbence spectrum based on integration area of UVA1; and calculating the PFA-PPD in vitro.

9 Claims, 4 Drawing Sheets

US 7,033,577 B2

IN VITRO PREDICTION OF SUNSCREEN PFA VALUES

RELATED APPLICATIONS

This patent application claims priority to Provisional Patent Application Ser. No. 60/447,092 filed Feb. 13, 2003 and Provisional Patent Application Ser. No. 60/506,833 filed on Sep. 29, 2003, with both applications being incorporated by reference herein.

BACKGROUND OF THE INVENTION

1. Field of the Invention

The invention relates generally to the in vitro prediction of a composition's sunscreen PFA values. More particularly, the present invention relates to an in vitro method for the prediction of in vivo UVA protection by a composition with sunscreen properties.

2. Description of Related Art

It is known that the UV portion of sunlight causes skin damage. UVB irradiation is almost entirely absorbed by the epidermis and it causes an erythemal or sunburn reaction, as well as induces DNA mutations.

UVA irradiation is capable of reaching dermal layers and even affecting circulating blood cells. Compared with UVB, UVA generates more oxidative stress, which induces matrix metalloproteases and suppresses skin immune function.

Sunscreen compositions or any compositions with sunscreen active material are designed to protect skin from photodamage that may result from UV light exposure. It is becoming more important to develop sunscreens that effectively protect from both UVB and UVA.

UVB protection of a sunscreen is measured by a FDA approved SPF in vivo method that utilizes erythema as a biological endpoint. In contrast to the SPF method there is no official method to measure photoprotection against UVA. At the same time, effective protection against the UVA portion of the solar spectrum associated with cumulative skin damage is an important element of sunscreen and anti-aging cosmetic formulations.

The JCIA (Japan Cosmetic Industry Association) method is an in vivo method that is the most often used in the U.S. According to this method, Protection Factor A (PFA) based on persistent pigment darkening (PPD) can determine UVA protection provided by sunscreens. It was adopted by JCIA in 1995 as an official method. Additional methods modeled after the JCIA method are described in *The Reproducibility of an In-Vitro Determination of the UVA INDEX Describing the Relative UVA Protection of Sun Care Products*, Gers-Barlag et al., IFSCC Magazine, Vol. 5, No.3, 2002; and *A New In-Vitro Test Method to Assess the UVA Protection Performance of Sun Care Products*, V. Wendel et al., SOFW 2001, 127.

Since PPD is produced in the basal keratinocytes by a photochemical conversion of preexisting melanin and its precursors and/or migration of melanosomes, it may be assumed that PPD gives a direct estimate of the UVA impact on the viable epidermis. PPD is a stable skin response that is linearly dependent on the amount of UVA that enters the viable epidermis. In the JCIA method, the PFA is determined from the ratio of the sunscreen-protected minimal PPD to the unprotected PPD, evaluated 2 to 4 hours after UVA exposure. This method utilizes a xenon arc light simulator filtered with a 2 millimeter (mm) WG335 and 1 mm UG11 filters and volunteers with skin types II, III and IV.

Time of UVA exposure during in vivo PFA testing of a sunscreen is based, according to the test protocol, on its PFA estimated value that was determined in vitro prior to the human tests. Thus, correct in vitro prediction of the PFA range of the test product is absolutely essential for the accuracy of in vivo tests and must be given to the testing lab prior to the study on volunteers. In the prior art methods, in vitro UVA protection is calculated using the integration area of normalized spectrum of a sunscreen in entire UVA region (UVA1+UVA2), which does not result in the accurate prediction of in vitro PFA values.

To overcome the deficiencies and inaccuracies associated with the prior art methods, the present invention provides a method for accurately predicting the in vitro PFA range for suncare compositions.

SUMMARY OF THE INVENTION

It is an object of the present invention to provide an in vitro method for prediction of in vivo UVA protection provided by sunscreens.

It is another object of the present invention to provide such a method that is reproducible.

It is yet another object of the present invention to provide such a method that correlates well with in vivo results.

These and other objects are achieved by an in vitro method for the prediction of in vivo UVA protection by a composition with sunscreen properties. The method includes the steps of: determining in vivo SPF; determining in vitro SPF based on the sunscreen's absorbance spectrum in the UV region; normalizing (adjusting) the absorbance spectrum of a sunscreen to correspond to its in vivo SPF; and calculating the PFA-PPD in vitro based on the integration area of normalized absorbance spectrum of a sunscreen in UVA1 region.

The terms "suncare composition" and "sunscreen composition" in the context of this application are meant to be interchangeable and include not only sunscreen compositions, but any compositions having one or more sunscreen actives. Other such compositions may include, but are not limited to, cosmetics, insect repellants, lip balms, shampoos, conditioners, gels, topical lotions, and the like.

DETAILED DESCRIPTION OF THE INVENTION

Figure 1:
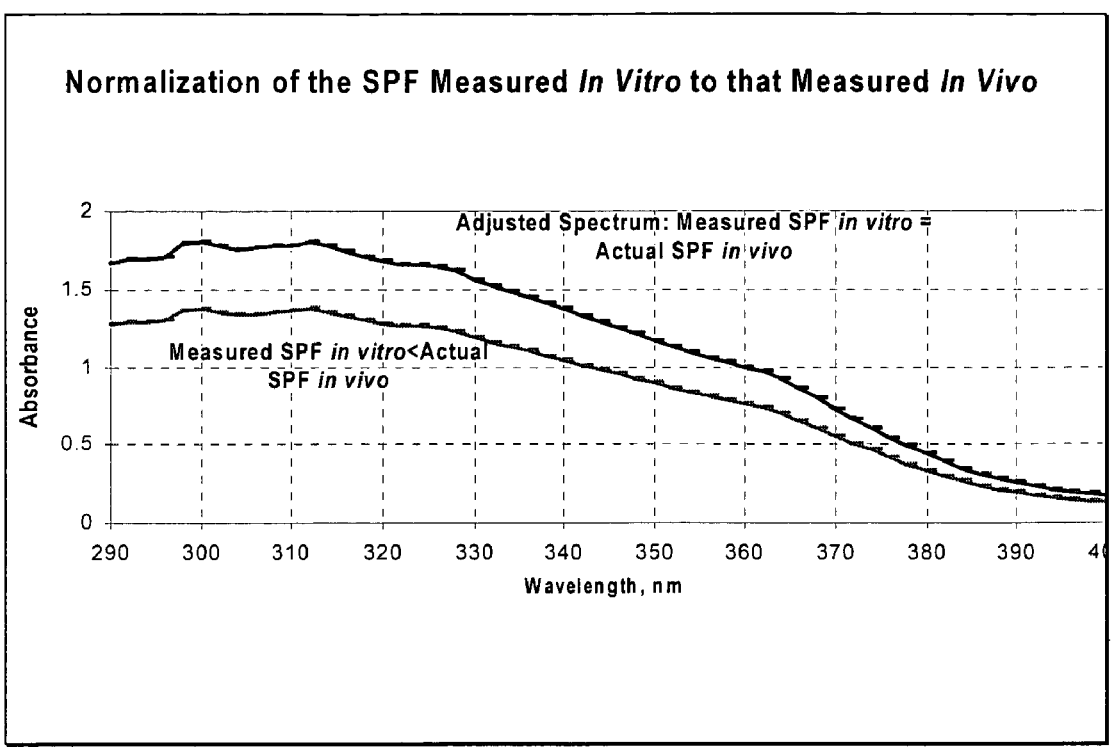
FIG. 1 is a graphical representation of the normalization of the SPF measured in vitro to that SPF measured in vivo.

The present invention provides an accurate method for predicting in vitro PFA values in sunscreen compositions. The method includes the steps of: determining in vivo SPF; determining in vitro SPF based on the sunscreen's absorbence spectrum in the UV region; normalizing the absorbence spectrum; and calculating the PFA-PPD in vitro based on the integration area of normalized absorbance spectrum of a sunscreen in UVA1 region.

To obtain in-vitro prediction for PFA-PPD values of a sunscreen composition the method of the present invention, including the steps set forth below, is employed.

Step 1. Determine in-vivo SPF for test formulation on at least 5 panelists.

The determination is based on the method outlined in the Food and Drug Administration (FDA) Final Monograph for sunscreen testing published in the Federal Register, Vol. 64, No. 98, May 21, 1999, which is incorporated by reference herein.

Step 2. Determine in-vitro SPF of sunscreen based on its absorbance spectrum in UV region.

This step may be conducted by any suitable method known in the art. By way of example, a suitable method includes, but is not limited to, the method described in SPF Analysis of Sunscreens, Technical Note for Labsphere UV-1000S UV Transmittance Analyzer, which is incorporated by reference herein.

The type of substrate and the application dose applied to the substrate have been unexpectedly found to be important factors in the accuracy of in vitro measurements of sunscreen absorbance spectra. In addition, it is preferred that the irradiance spectrum of the lamp source used reflect the irradiance spectrum used in the lamp source used in the in-vivo SPF test, as described in Step 1 above.

To achieve the most accurate measurements, the substrate used in the present invention should closely resemble mammalian skin. Therefore, the substrate should be transparent to UV light and simulate the porosity and texture of skin. Suitable substrates for use in the invention may include, but are not limited to, surgical tape such as 3M Transpore™, polyvinyl chloride film such as Saran Wrap®, and synthetic skin substitute material such as Vitro-Skin®. Preferably the substrate used in the present invention is Vitro-Skin®.

Properly selecting the application dose of the sunscreen composition to be applied to the substrate is also important. It has been found that the use of an application dose of 2 mg/cm$^2$, which corresponds to the application dose used during in-vivo PFA (PPD, JCIA) and also during in vivo SPF tests, provides the most accurate results in determining in vitro PFA.

In a preferred embodiment of the present invention, a Labsphere UV-1000S Transmittance Analyzer was used in conjunction with Vitro-Skin® as the substrate and a sunscreen application dose of 2 mg/cm$^2$.

Step 3. If the in-vitro SPF differs from the label SPF, the adjustment of the absorbance spectrum is needed to normalize it to the label value obtained in vivo. Equation 1 is used to normalize the absorbance spectrum.

Equation 1:

$$SPF \text{ in vivo} = SPF \text{ in vitro} = \frac{\int_{290nm}^{400nm} E(\lambda) \cdot S(\lambda)}{\int_{290nm}^{400nm} E(\lambda) \cdot S(\lambda) / 10^{[A(\lambda) \cdot C]}}$$

Where:
$E(\lambda)$=irradiance at wavelength $\lambda$ of the light spectrum used
$S(\lambda)$=effectiveness of a biological endpoint at wavelength $\lambda$
Note: for the SPF it is erythema action spectrum
$A(\lambda)$=absorbance
$C$=constant factor for the adjustment of the spectrum This eliminates the impact of the application technique on the absorbance spectrum of a sunscreen. During this mathematical adjustment, only the height of the sunscreen's absorbance spectrum is adjusted by a scalar multiplier in an iterative method to correspond to its in vivo (ACTUAL) SPF value.

The convolution spectrum was calculated by multiplying the irradiation spectrum with CIE UV hazard spectrum. The sunscreen absorbance spectrum is then incorporated into the convolution spectrum in order to obtain in vitro SPF. The configuration of the spectrum reflecting the specific sunscreen composition remains unchanged. This "normalization" also takes into the account, at least partially, the implications of possible photo-instability of the sunscreen during its PFA study.

FIG. 1 demonstrates the normalization of the SPF measured in vitro to that SPF measured in vivo.

If the in vitro SPF is equal to the in vivo SPF then no adjustment or normalization is needed because in this case C=1 and the integration area of the absorbance spectrum of sunscreen in UVA1 (340–400 nm) region "as is" can be used for in vitro estimation of the PPD value.

Step 4. Calculate PFA-PPD in vitro using equation 2 set forth below.

Equation 2:

$$PFA - PPD \text{ in vitro} = \frac{\int_{340nm}^{400nm} E(\lambda) \cdot S(\lambda)}{\int_{340nm}^{400nm} E(\lambda) \cdot S(\lambda) / 10^{[A(\lambda) \cdot C]}}$$

Where:
$E(\lambda)$=irradiance at wavelength $\lambda$ of the light spectrum used
$S(\lambda)$=effectiveness of a biological endpoint at wavelength $\lambda$
Note: for the PPD prediction it is PPD action spectrum
$A(\lambda)$=absorbance
$C$=constant factor for the adjustment of the spectrum as in Eq. 1.

It is preferred that the irradiance spectrum of the lamp source used reflect the irradiance spectrum used in the lamp source used in the lab PFA testing.

In addition, an important consideration when predicting the PFA values of a sunscreen composition is the effects of UVA2 (320–340 nm) and UVA1 (340–400 nm) on skin. Careful examination of the effects of UVA on the skin and underlying structures has led to the division of the spectrum into two subsets, namely UVA2 (320–340 nm) and UVA1 (340–400 nm).

UVA radiation can cause two types of damage depending on the wavelength band. UVB and UVA2 light cause erythema (sunburn) and raise the risk of skin cancer far more than UVA1. UVA1 activates skin enzymes that break down collagen and also activates photoactive molecules in the cell that in turn damage the DNA. UVA1 plays an important role in photoageing, especially wrinkling and sagging of the skin. Recent studies show that UVA2 is responsible for the suppressing established immune reactions. On the other hand, no immune suppression was noted after irradiation with UVA1 only.

Figure 2:
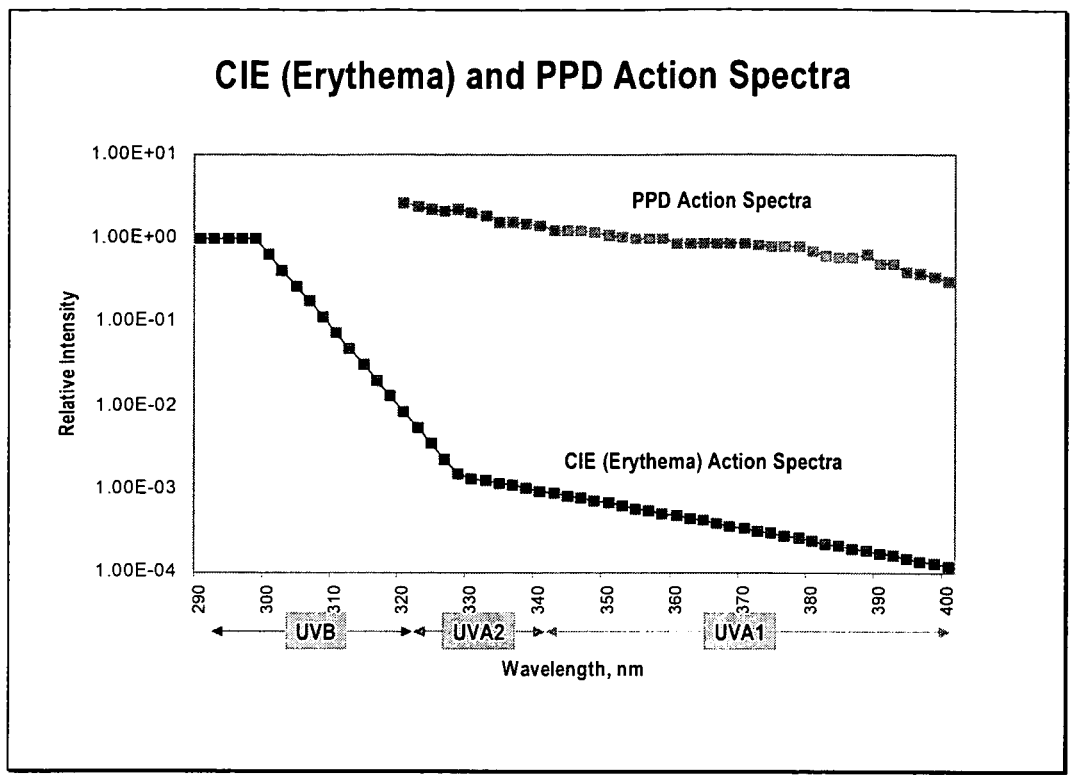
FIG. 2 is a graphical representation of a comparison of Commission International de L'Eclairage (CIE) UV Hazard (erythemal) and PPD action spectra.

As demonstrated in FIG. 2, a comparison of CIE UV Hazard (Erythemal) and PPD action spectra also shows the difference between skin biological response plotted against photon energy in UVA1 and UVA2 areas.

It is the UVA1 region of spectrum that produces a tanning (PPD) response. Therefore, since the PFA prediction is based on the PPD, as evident in equation 2 above, the method of the present invention uses only the UVA1 spectrum to measure the PFA. As a result, the prediction of the PFA values in sunscreen compositions is highly accurate.

In lieu of the above, unexpected findings, in a preferred embodiment of the present invention, when calculating the PFA-PPD$_{in\ vitro}$, the integration area of "normalized" absorbance spectrum of sunscreen in the UVA1 (340–400 nm) spectrum is used in conjunction with a xenon arc 150 wt lamp filtered with 2 mm WG355 and 1 mm UG11, and the PPD action spectrum (FIG. 2).

In a preferred embodiment, step 2 through step 4 is repeated at least five times. From the set of calculated in vitro PFA-PPD's, the average and the standard deviation should be calculated. The lower bound (average minus three standard deviations) should be reported as the measured in vitro PFA-PPD.

EXAMPLES

The proposed method has been evaluated in PFA (PPD) studies of fifteen commercially available sunscreens, set forth in Table 1 below. Tested sunscreens contained various combinations of FDA approved organic and inorganic sunscreen actives.

TABLE 1

In Vitro/In Vivo Data

| | | | In vitro Prediction Based on: | |
|---|---|---|---|---|
| Product | SPF | PFA - PPD, JCIA | UVA1 & UVA2 | UVA1 |
| 1 | 50 | 8.66 | 12.08 | 9.42 |
| 2 | 30 | 9.49 | 11.77 | 9.41 |
| 3 | 50 | 13.07 | 17.54 | 13.03 |
| 4 | 50 | 8.3 | 11.9 | 9.4 |
| 5 | 30 | 6.33 | 9.05 | 7.82 |
| 6 | 35 | 9.74 | 14.77 | 12.5 |
| 7 | 30 | 8 | 11.2 | 9.5 |
| 8 | 50 | 12.5 | 15.2 | 11.71 |
| 9 | 50 | 5.66 | 9.84 | 8.39 |
| 10 | 30 | 3.16 | 4.2 | 3.5 |
| 11 | 30 | 3.04 | 4 | 3.4 |
| 12 | 45 | 16.32 | 21.09 | 17.08 |
| 13 | 50 | 7.07 | 9.99 | 8.02 |
| 14 | 45 | 5.07 | 7.85 | 6.14 |
| 15 | 20 | 5.82 | 7.81 | 6.19 |

It was found that integration area of 340–400 nm (UVA1) utilized in the proposed method provides better in vitro/in vivo correlation as compared to the integration area of 320–400 nm (UVA1 and UVA2) and is aligned with existing knowledge regarding skin biological responses to the irradiation by UVA1 and UVA2 wavelength bands.

Figure 3:
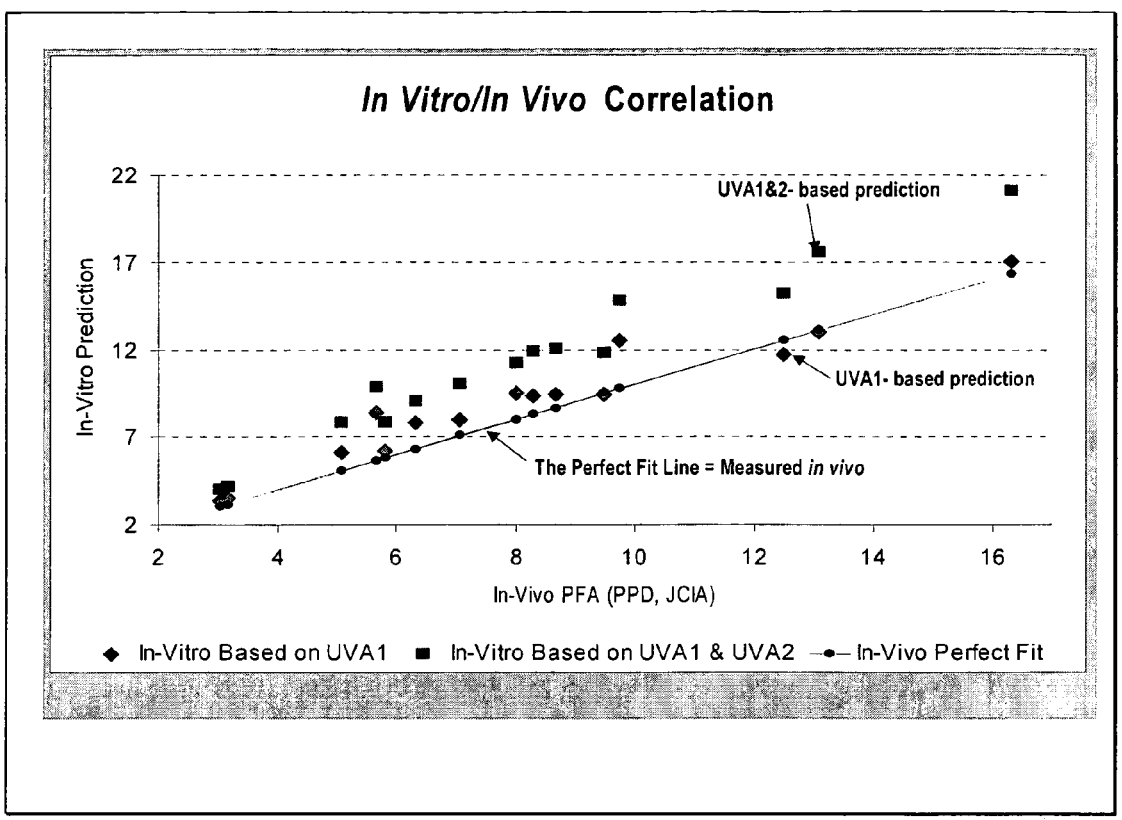
FIG. 3 is a graphical representation of the correlation between in vitro/in vivo predictions based on both the UVA1 integration area and the UVA1+UVA2 integration area.

As demonstrated in FIG. 3, the statistical comparisons of the two methods with the perfect fit (=PFA measured in vivo) indicated that the in vitro method based on integration area of UVA1 only gives a better fit (sum of squared residuals of 24.97) than the in vitro method based on both UVA1 and UVA2 (sum of squared residuals of 162.5).

Figure 4:
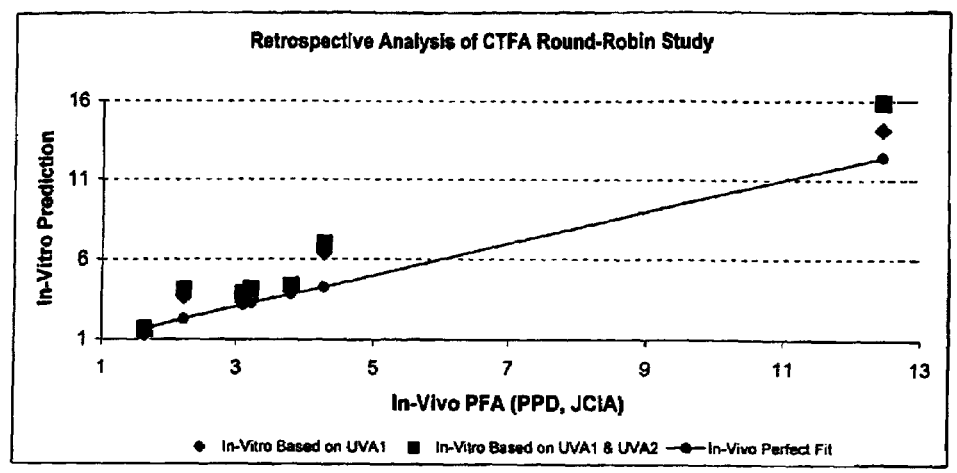
FIG. 4 is another graphical representation of the correlation between in vitro/in vivo predictions based on both the UVA1 integration area and the UVA1+UVA2 integration area.

The method of the present invention has also been evaluated against seven CTFA products, as set forth below in table 2, and has also confirmed that in vitro prediction based on integration area of UVA1 only gives a better fit. This is demonstrated in FIG. 4.

TABLE 2

| | | In vitro Prediction Based on: | |
|---|---|---|---|
| Product & Label | In vivo PPD, JCIA | UVA1&UVA2 | UVA1 |
| CTFA "A" SPF 17.27 | 3.21 | 4.15 | 3.48 |
| CTFA "E" SPF 8.4 | 1.65 | 1.61 | 1.38 |
| CTFA "F" SPF 9.5 | 3.09 | 3.9 | 3.28 |
| CTFA "G" SPF 13.3 | 4.27 | 7.04 | 6.4 |
| CTFA "H" SPF 5 | 3.8 | 4.4 | 4.25 |
| CTFA "I" SPF 13.9 | 2.23 | 4.12 | 3.64 |
| CTFA "J" SPF 30.7 | 12.43 | 15.9 | 14.16 |

Overall, it appears that this method is equally applicable to the sunscreens with low, medium and high PFA (PPD) values containing wide range of actives.

In vitro prediction of in vivo UVA protection provided by sunscreens according to the present invention can be successfully utilized as a preliminary step before PFA (PPD, JCIA) tests, which will provide excellent in vitro/in vivo correlation; save time and resources; serve as an optimization tool for sunscreen development and evaluation; and for benchmarking.

A similar approach to that of the present invention may be applied for in vitro determination of a sunscreens' protection potential against other types of UV damage by utilizing various action spectra, irradiation spectrum of the specific light source and integration areas that are relevant to the test conditions.

It should be understood that the foregoing description is only illustrative of the present invention. Various alternatives and modifications can be devised by those skilled in the art without departing from the invention. Accordingly, the present invention is intended to embrace all such alternatives, modifications and variances.

We claim:

1. A method for predicting the PFA value of a sunscreen composition comprising the steps of:
   determining in vivo SPF;
   determining in vitro SPF based on an absorbance spectrum in a UV region for said sunscreen composition; and
   calculating the PFA-PPD in vitro based on an integration area of a UVA1 region.

2. The method of claim 1, further comprising, after the step of determining in vitro SPF, the step of normalizing said absorbance spectrum.

3. The method of claim 1, wherein said step of determining in vitro SPF is conducted on a substrate selected from the group consisting of surgical tape, polyvinyl chloride film, and synthetic skin substitute material.

4. The method of claim 1, wherein said step of determining in vitro SPF is conducted on a substrate formed of a synthetic skin substitute material.

5. The method of claim 1, wherein said step of determining in vitro SPF comprises a sunscreen composition applied to a substrate in an application dose of 2 mg/cm$^2$.

6. The method of claim 3, wherein said step of determining in vitro SPF comprises a sunscreen composition applied to said substrate in an application dose of 2 mg/cm$^2$.

7. The method of claim 4, wherein said step of determining in vitro SPF comprises a sunscreen composition applied to said substrate in an application dose of 2 mg/cm$^2$.

8. The method of claim 1, wherein said PFA-PPD in vitro is calculated using an equation:

$$PFA - PPD \text{ in vitro} = \frac{\int_{340 \text{ nm}}^{400 \text{ nm}} E(\lambda) \cdot S(\lambda)}{\int_{340 \text{ nm}}^{400 \text{ nm}} E(\lambda) \cdot S(\lambda) / 10^{[A(\lambda) \cdot C]}}$$

wherein $E(\lambda)$ is an irradiance at a wavelength $\lambda$ of a light spectrum used, $S(\lambda)$ is an effectiveness of a biological endpoint at a wavelength $\lambda$, $A(\lambda)$ is an absorbance, and C is a constant factor for an adjustment of the light spectrum.

9. The method of claim 2, wherein said absorbance spectrum is normalized using an equation:

$$SPF \text{ in vivo} = SPF \text{ in vitro} = \frac{\int_{290 \text{ nm}}^{400 \text{ nm}} E(\lambda) \cdot S(\lambda)}{\int_{290 \text{ nm}}^{400 \text{ nm}} E(\lambda) \cdot S(\lambda) / 10^{[A(\lambda) \cdot C]}}$$

wherein $E(\lambda)$ is an irradiance at a wavelength $\lambda$ of a light spectrum used, $S(\lambda)$ is an effectiveness of a biological endpoint at a wavelength $\lambda$, $A(\lambda)$ is an absorbance, and C is a constant factor for an adjustment of the light spectrum.

* * * * *